(12) United States Patent
Heisig et al.

(10) Patent No.: US 8,455,551 B2
(45) Date of Patent: Jun. 4, 2013

(54) BROAD SPECTRUM DISINFECTANT

(75) Inventors: Christopher C. Heisig, Saint Louis, MO (US); Thomas W. Smith, Saint Louis, MO (US); Peter N. Karanja, Saint Louis, MO (US); Nancy-Hope E. Kaiser, Pontoon Beach, IL (US)

(73) Assignee: American Sterilizer Company, Mentor, OH (US)

( * ) Notice: Subject to any disclaimer, the term of this patent is extended or adjusted under 35 U.S.C. 154(b) by 136 days.

(21) Appl. No.: 12/932,751

(22) Filed: Mar. 4, 2011

(65) Prior Publication Data

US 2012/0225948 A1     Sep. 6, 2012

(51) Int. Cl.
*A61K 31/14* (2006.01)
(52) U.S. Cl.
USPC .......................................................... 514/642
(58) Field of Classification Search
USPC .......................................................... 514/642
See application file for complete search history.

(56) References Cited

U.S. PATENT DOCUMENTS

| | | |
|---|---|---|
| 5,389,685 A | 2/1995 | Smith et al. |
| 5,454,983 A | 10/1995 | Michael et al. |
| 5,454,984 A | 10/1995 | Graubart et al. |
| 5,925,681 A | 7/1999 | Crisanti et al. |
| 5,948,741 A | 9/1999 | Ochomogo et al. |
| 5,948,742 A | 9/1999 | Chang et al. |
| 5,965,514 A | 10/1999 | Wierenga et al. |
| 5,972,876 A | 10/1999 | Robbins et al. |
| 6,096,701 A | 8/2000 | Mondin et al. |
| 6,159,916 A | 12/2000 | Robbins et al. |
| 6,200,941 B1 | 3/2001 | Strandburg et al. |
| 6,214,784 B1 | 4/2001 | Robbins et al. |
| 6,242,402 B1 | 6/2001 | Robbins et al. |
| 6,287,585 B1 | 9/2001 | Johansen |
| 6,616,922 B2 | 9/2003 | Taylor et al. |
| 6,927,237 B2 | 8/2005 | Hei et al. |
| 7,387,990 B2 * | 6/2008 | Dettmann et al. ............. 510/384 |
| 7,576,047 B2 | 8/2009 | Kilkenny et al. |
| 7,741,263 B2 | 6/2010 | Kilkenny et al. |
| 2002/0035053 A1 | 3/2002 | Demeyere et al. |
| 2002/0103098 A1 | 8/2002 | Harrison et al. |
| 2003/0064910 A1 | 4/2003 | Fong et al. |
| 2007/0117957 A1 | 5/2007 | Mullen |
| 2010/0055198 A1 | 3/2010 | Wang et al. |

FOREIGN PATENT DOCUMENTS

WO     WO 97/34990 A1     9/1997

* cited by examiner

*Primary Examiner* — Rei-tsang Shiao
(74) *Attorney, Agent, or Firm* — Hudak, Shunk & Farine Co. LPA

(57) ABSTRACT

A broad spectrum disinfectant includes a quaternary ammonium halogen, an alkaline agent, a chelating agent, a nonionic surfactant coupler, at least one alkoxylated nonionic surfactant, and water or any aliphatic alcohol. The disinfectant composition is phenol-free, is effective in eradicating microorganisms such as various fungi, and is stable to gamma-irradiation.

19 Claims, 3 Drawing Sheets

BROAD SPECTRUM DISINFECTANT

FIELD OF THE INVENTION

The present invention relates to a phenol-free broad spectrum disinfectant composition that is effective in eradicating microorganisms. More specifically, the present invention relates to an alkyl ammonium halogen disinfectant that typically does not eradicate microorganisms such as *Aspergillus niger* and *Aspergillus brasiliensis* but, in association with compounds comprising a solvent, an alkaline agent, a chelant, a nonionic surfactant coupler, and wetting and emulsifying surfactants, surprisingly is very effective in eradicating the above-noted fungi, as well as many other organisms.

BACKGROUND OF THE INVENTION

Quaternary ammonium chloride-containing products (also known as "quats") have been used in hard surface disinfection for many years. As a broad-spectrum disinfectant, they have acceptable efficacy against some organisms (e.g. *Staphylococcus aureus*), but often fall short in efficacy against many spore-forming fungi. Two particularly difficult to kill organisms for these types of disinfectants are *Aspergillus niger* and *Aspergillus brasiliensis*. Thus, other harsher disinfectant or sporicidal products, such as phenols, bleach (sodium hypochlorite) and peracetic acid are often used when fungal efficacy is required.

For use in aseptic environments (e.g. Clean Room Class 100), the disinfectant chemistries often need to be sterile. The most commonly accepted form of terminal sterilization for this application is gamma-irradiation.

Various compounds are not desired or acceptable either from a regulatory standpoint in some countries, such as $C_8$-$C_9$ aliphatic quaternary ammonium chloride, and or they degrade upon exposure to gamma-irradiation, such as aromatic quaternary ammonium chloride compounds. Quat products also traditionally have poor fungicidal efficacy. Various chelating agents such as Tetrasodium ethylenediaminetetraacetate (EDTA), a chelating agent commonly found in many disinfectant products, are not acceptable in many European countries.

To achieve acceptable fungicidal activity, many phenolic or oxidizing agent-containing products are used. However, these products have draw-backs of their own including strong odor and mucous membrane irritation, material incompatibility issues, and requirements for overly cumbersome personal protective equipment (PPE) during use.

U.S. Pat. No. 5,454,984 relates to cleaning composition containing an aqueous solution, a quaternary ammonium compound component, a nonionic surfactant component, and a glycol ether solvent that functions at a low level of the quaternary ammonium compound component while allegedly maintaining at least one of the following desirable properties, an acceptable cleaning efficacy, a low level irritation or toxicity profile, and/or a broad spectrum antimicrobial activity.

U.S. Pat. No. 5,925,681 relates to concentrated aqueous liquid disinfectant compositions that exhibit a blooming effect when diluted in a larger volume of water. The concentrate compositions include non-phenolic constituents to provide a disinfecting effect, and are non pine-oil containing. Working strength dilutions of the concentrated aqueous liquid disinfectant compositions are allegedly effective against gram positive type pathogenic bacteria such as *Staphylococcus aureus* as well as gram negative type pathogenic bacteria such as *Salmonella choleraesuis*.

U.S. Pat. No. 6,616,922 relates to antibacterial compositions having alleged antibacterial effectiveness. The antibacterial compositions contain an antibacterial agent, an alkamine oxide, a nonionic and/or cationic cosurfactant, an optional polymeric thickener, and water.

U.S. Pat. No. 6,927,237 relates to two-solvent antimicrobial compositions and methods employing these two solvent compositions. The two solvent compositions typically contain a second solvent that is not or is only sparingly soluble in a diluting solvent. The two-solvent composition can form a clear single-phase solution. The two-solvent antimicrobial compositions allegedly reduce the population of microbes on various surfaces such as facilities, containers, or equipment found in food, beverage, or pharmaceutical industries at temperatures between about −70° C. to about 100° C.

WO Publication 97/34990 relates to a cleaner concentrate composition which can be diluted to form a viscous use solution, the cleaner composition comprising: an ammonium compound and/or an amphoteric compound and an anionic surfactant, wherein the composition is free of amine oxide.

SUMMARY OF THE INVENTION

An alkyl ammonium halogen compound in combination with compounds such as a chelant, for example an alkylglycine dicarboxylic acid, an iminodisuccinic acid, an ethylenediaminedisuccinate, or a carboxylmethyl inulin; various nonionic coupling or hydrotrope surfactants such as an alkylamine oxide; various alkoxylated nonionic surfactants such as one or more amine alkoxylates, or one or more alcohol alkoxylates, or one or more ethylene oxide-propylene oxide block copolymers; various solvents; and an alkaline agent; in an alkali medium have been found to be very effective in destroying a wide range of microorganisms including fungi. The disinfectant composition is generally compliant with current US EPA regulations as well as various current European regulations such as BPD (Biocidal Product Directive) and REACh (Registration, Evaluation, Authorization, and Restriction of Chemical substances). Another important aspect is that the composition is free of phenol and EDTA. The compositions of the present invention relate to an essential balance of various components that achieve unexpected disinfection capabilities with regard to eradicating a broad spectrum of microorganisms and are stable to gamma-irradiation allowing them to be sold as sterile products.

In one aspect of the invention, a broad spectrum liquid cleaning composition, comprises a quaternary ammonium halogen; an alkaline agent; a chelant; a nonionic surfactant coupler; at least one alkoxylated nonionic surfactant; and a solvent system comprising water, or an aliphatic alcohol, or both.

Another aspect of the present invention relates to a process for forming a broad spectrum liquid cleaning composition, comprising the steps of: mixing in any order a quaternary ammonium halogen; an alkaline agent; a chelant; a nonionic surfactant coupler; at least one alkoxylated nonionic surfactant; and a solvent system comprising water, or an aliphatic alcohol, or both.

DETAILED DESCRIPTION OF THE INVENTION

Figure 1:
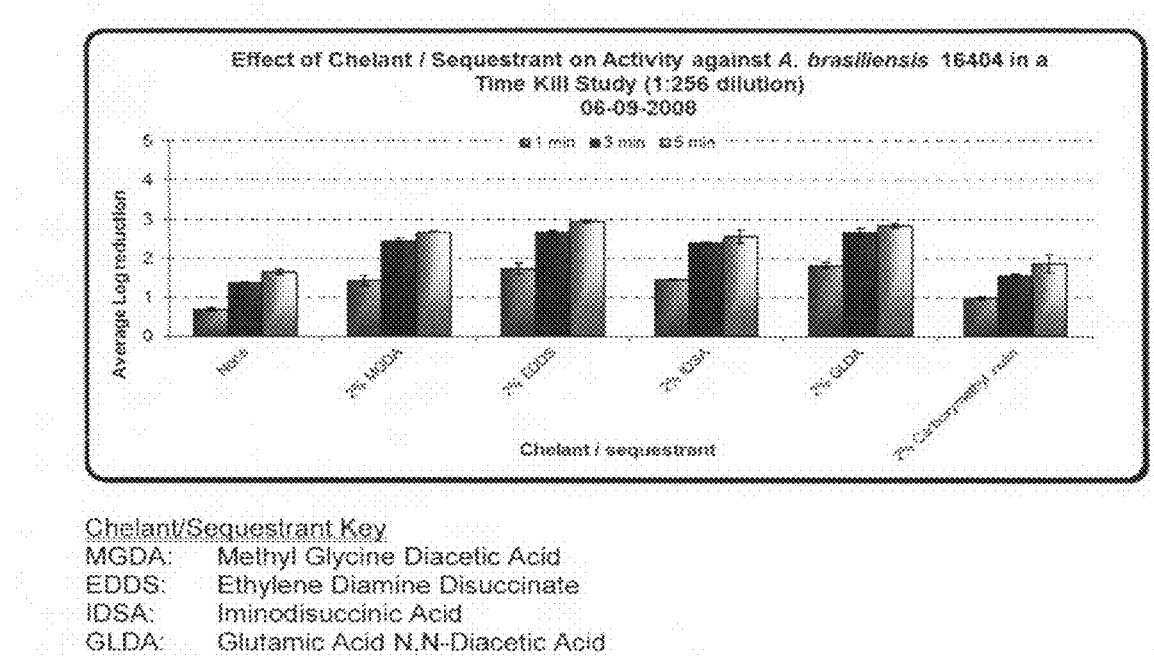
FIG. 1 is a chart showing the effect of different chelating agents/sequestrants with regard to their efficacy against *Aspergillus brasiliensis* 16404.

The quaternary ammonium halogens of the present invention are generally alkyl ammonium chloride compounds wherein one or more of the alkyl groups can be different from the others. Useful quaternary ammonium disinfectants have a general structural formula:

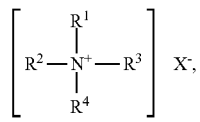

wherein $X^-$ is a halogen and preferably chlorine, wherein each $R^1$ and $R^2$, independently, is an alkyl having from 1 to about 7 carbon atoms, desirably from 1 to about 3 carbon atoms, and preferably 1 or 2 carbon atoms, wherein each $R^3$ and $R^4$, independently, is an alkyl having from about 8 to about 25 carbon atoms, desirably from about 9 to about 20 carbon atoms, and preferably from about 10 or about 12 to about 15 or about 18 carbon atoms, or is an alkyl aryl or an aryl alkyl such as benzyl having a total of from about 6 to about 20 carbon atoms, desirably from about 6 to about 15 and preferably from about 6 to about 12. The various R groups are saturated. If stability with regard to gamma irradiation is desired, the aromatic quats are not utilized.

Examples of suitable quaternary ammonium disinfectants include dioctyl and didecyl dimethyl ammonium chloride, N-alkyl($C_{12}$ to $C_{18}$)dimethyl benzyl ammonium chloride, and N-alkyl($C_{12}$ to $C_{18}$)dimethyl ethylbenzyl ammonium chloride, and mixtures thereof. These disinfectants are preferably used herein at a pH of about 7 to about 13 and desirably from about 9 to about 13 and preferably from about 10 to about 12. A highly preferred quaternary ammonium disinfectant is didecyl dimethyl ammonium chloride (DDAC). A distinct advantage of DDAC is that it is stable to gamma-radiation, is registered with the US EPA and is supported by the BPD. DDAC is available as Bardac 2280® from Lonza, Inc. of Fairlawn, N.J. supplied as an 80% active raw material, generally 10% ethanol and generally 10% water by weight. It is also available as BTC-1010 80% from Stepan Company, Northfield, Ill. The amount of the active or per se quaternary disinfectant compound of the present invention generally varies from about 5 wt. % to about 25 wt. %, desirably from about 7 wt. % to about 15 wt. % or about 20 wt. %, and preferably from about 8 wt. % to about 12 wt. % based upon the total weight of all set forth components of the broad spectrum cleaning composition of the present invention including any carriers and water.

The alkaline agent component serves as a source of alkalinity and also adds buffering capability to the composition. Suitable alkaline agents include an organic alcohol amine such as monoethanolamine and triethanolamine, various strong bases such as sodium hydroxide or potassium hydroxide, and other basic compounds such as sodium carbonate, sodium bicarbonate, and the like. The amount of such alkaline agents is from about 3 wt. % to about 10 wt. %, desirably from about 4 wt. % to about 9 wt. %, and preferably from about 5 wt. % to about 8 wt. % based upon the total weight of all set forth components of the broad spectrum cleaning composition of the present invention including any carriers and water.

Generally the pH of the cleaning composition is as noted above, that is from about 7 to about 13, desirably from about 9 to about 13 and preferably from about 10 to about 12.

An aliphatic alcohol component is utilized as a cosolvent inasmuch as it aids in the solubility of the system. Suitable aliphatic alcohols have from 2 to about 8 carbon atoms and desirably from 2 to about 4 carbon atoms and include ethanol, isopropyl alcohol, butanol, with n-propyl alcohol being preferred. The amount of the one or more alcohols is generally from about 2 wt. % to about 10 wt. % or 20 wt. %, desirably from about 3 wt. % to about 9% and preferably from about 4 wt. % to about 7 wt. % based upon the total weight of all set forth components of the broad spectrum cleaning composition of the present invention including any carriers and water.

A chelating/sequestering agent is utilized since it aids in the efficacy of the cleaning composition in hard water. That is, the chelating agent will interact with metal ions that the cleaning composition comes into contact with during use. The chelant is desirably biodegradable. Suitable chelants include alkylglycine organic acids such as methylglycine diacetic acid and derivatives thereof. Examples of other suitable chelants include iminodisuccinic acids and derivatives thereof such as the Baypure CX series from Lanxess, various ethylenediaminedisuccinates and derivatives thereof such as the Natrlquest series from Innospec, and various carboxymethyl inulin and derivatives thereof such as the DeQuest series from Solutia. Methylglycine diacetic acid is preferred such as the sodium salt thereof. This compound is available as Trilon M from BASF in liquid form containing 40 wt. % of the chelating agent as the active component. Suitable amounts of the active or per se chelating agent range from about 0.2 wt. % to about 2 wt. % or 3 wt. %, desirably from about 0.6 wt. % to about 1.6 wt. %, and preferably from about 0.8 wt. % to about 1.4 wt. % based upon the total weight of all set forth components of the broad spectrum cleaning composition of the present invention including any carriers and water.

Another component of the broad spectrum cleaning liquid composition of the present invention are various surfactants such as nonionic coupling agents or hydrotropes such as various alkylamine oxides having a total of from about 6 to about 14 carbon atoms with a preferred example being octyldimethylamine oxide, e.g. Mackamine C8 from Rhodia wherein the octyldimethylamine active content is 40 percent by weight. A purpose of this nonionic coupling agent or hydrotrope is to keep the applicable system components, especially the chelant, solubilized in the concentrate composition. The amount of the one or more nonionic coupling and/or hydrotrope compounds is generally from about 0.2 wt. % to about 5 wt. %, desirably from about 0.5 wt. % to about 3.0 wt. % and preferably from about 0.75 wt. % to about 1.5 or about 2.5 wt. % based upon the total weight of all set forth components of the broad spectrum cleaning composition of the present invention including any carriers and water.

Another important component of the broad spectrum cleaning composition of the present invention is one or more alkoxylated, preferably amine alkoxylated nonionic surfactants having good high and/or low HLB values to provide a suitable balance of hydrophilicity to hydrophobicity. Another option is an EO/PO block copolymer. Nonionic alkoxylated, preferably amine alkoxylated surfactants having from about 2 to about 20 and desirably from about 2 to about 15 repeat units of an alkylene oxide, with propylene oxide and ethylene oxide being preferred, are desired since they contribute to the wetting and rinsability of a surface treated with the cleaning composition of the present invention. Although only a high HLB surfactant can be utilized or only a low HLB (hydrophilic-lipophilic balance) surfactant can be utilized, it is preferred that both a high HLB and a low HLB surfactant be utilized together. The high HLB value is from about 12 to about 24, and desirably from about 14 to about 20. A preferred compound is coco amine 15 EO meaning that it is a coco amine ethoxylated with 15 moles of ethoxylation. This nonionic surfactant is available from Akzo Nobel as Ethomeen® C25A and has a HLB of 16.8. The low HLB nonionic surfactant can be coco amine 2 EO meaning that it is a coco amine ethoxylated with 2 moles of ethoxylation. This nonionic surfactant is also available from Akzo Nobel as Ethomeen® C12 and has an HLB of 6 but the HLB of such surfactants can vary from about 2 to about 11, and desirably from about 3 to about 8.

The amount of the high HLB compound per se is from about 0.2 wt. % to about 2.0 wt. %, desirably from about 0.3 wt. % to about 1.5 wt. % and preferably from about 0.4 wt. % to about 0.8 wt. % based upon the total weight of all set forth components of the broad spectrum cleaning composition of the present invention including any carriers and water. The amount of the low HLB compound is from about 0.2 wt. % to about 2.0 wt. %, desirably from about 0.3 wt. % to about 1.5 wt. % and preferably from about 0.4 wt. % to about 0.8 wt. % based upon the total weight of all set forth components of the broad spectrum cleaning composition of the present invention including any carriers and water. The overall amount of the one or more high HLB compounds and/or the one or more low HLB compounds is from about 0.4 to about 4.0, desirably from about 0.6 to about 3.0, and preferably from about 0.8 to about 1.6.

Other suitable nonionic surfactants are the various block copolymers of ethylene oxide and propylene oxide and the same are well known to the art and to the literature. The amount thereof is from about 0.4 wt. % to about 4.0 wt. % and desirably from about 0.6 wt. % to about 3.0 wt. %.

Still other alkoxylated nonionic surfactants that are acceptable include alcohol alkoxylated surfactants with varying moles of alkoxylation, such as ethoxylation therein such as from about 2 to about 15, and desirably from about 3 to about 12. Once again, it is preferred that both hydrophilic and hydrophobic compounds are used in combination. Examples of suitable alcohol alkoxylated surfactants include a secondary alcohol ethoxylate having 3 moles of ethoxylation; a secondary alcohol ethoylate having 5 moles of ethoxylation, a secondary alcohol ethoxylate having 7 moles of ethoxylation, et al. alkoxylated surfactants having ethylene oxide/proroylene oxide copolymer, $C_{9-11}$ alcohol ethoxylate having 2.5 moles of ethoyxlation, $C_{11}$ alcohol ethoxylate having 3 moles of ethoxylation, an alcohol ethoxylate having 8 moles of ethoxylation, an alcohol ethoxylate having 5 moles of ethoxylation, a $C_{9-11}$ alcohol ethoxylate having 4 moles of ethoxylation, a $C_8$ alcohol ethoxylate having 4 moles of ethoxylation, a $C_{9-11}$ alcohol ethoxylate having 2.5 moles of ethoxylation, and a $C_{9-11}$ alcohol ethoxylate having 5 moles of ethoxylation. Typical examples of commercial surfactants include: Tergitol 15-S-3, Tergitol 15-S-5, Tergitol 15-S-7, Tergitol L-61, Tomadol 91-2.5, Tomadol 1-3, Berol 508, Berol 505, Berol 260, Berol 840, Neodol 91-2.5, Neodol 91-5, Neodol 1-2.5, and Neodol 1-5. Tomadols are commercially available from Tomah Products Inc., Tergitols are commercially available from Dow, Berols are commercially available from Akzo Nobel, and Neodols are commercially available from Shell Chemical Company.

The amount of the one or more alcohol alkyoxlated nonionic surfactants is generally from about 0.1 wt. % to 10 wt. %, and desirably from about 0.5 wt. % to 5 wt. % based upon the total weight of all set forth components of the broad-spectrum cleaning composition of the present invention including any carriers and water.

An essential ingredient of the broad spectrum cleaning liquid composition of the present invention is water and preferably deionized water. The water should have a relatively low bioburden to maintain preservative effectiveness. The amount of the water as well as any carriers utilized with regard to various components of the present invention is such that the total amount of all of the components of the broad-spectrum cleaning composition of the present invention adds up to approximately 100 wt. %. Desirably the amount of water is a major component of the broad-spectrum cleaning composition as is apparent from Table A.

Example compositions, of the present invention are set forth in Table A.

TABLE A

| Chemical Name | Brand Name | Formula # A wt. % | B wt. % | C wt. % | D wt. % | E wt. % | F wt. % |
|---|---|---|---|---|---|---|---|
| Deionized water | Deionized water | 63.50 | 66.50 | 67.00 | 68.50 | 68.50 | 69.62 |
| Didecyl dimethyl ammonium chloride (80%) | Bardac 2280, BTC 1010-80% | 12.50 | 12.50 | 12.50 | 12.50 | 12.50 | 9.38 |
| Ethanol-amine | Mono-ethanolamine | 6.00 | 6.00 | 6.00 | 6.00 | 6.00 | 6.00 |
| n-Propyl alcohol | N-Propyl Alcohol | 5.00 | 5.00 | 5.00 | 5.00 | 5.00 | 5.00 |
| Methylglycine diacetic acid, sodium salt (40%) | Trilon M Liquid | 5.00 | 5.00 | 2.50 | 2.50 | 2.50 | 5.00 |
| Octyl-dimethylamine oxide (40%) | Mackamine C8 | 5.00 | 4.00 | 4.00 | 4.50 | 3.50 | 4.00 |
| Coco Amine 15EO | Ethomeen C25A | 0.50 | 0.50 | 0.50 | 0.50 | 0.50 | 0.50 |
| Coco Amine 2EO | Ethomeen C12 | 2.50 | 0.50 | 2.50 | 0.50 | 1.50 | 0.50 |

As apparent from Table A, if a component is supplied as part of a solution, the amount of the particular component, i.e. the active amount, is set forth in parentheses. Thus, while the total weight of the quat component is set forth as 12.5 wt. %, the actual weight of the quat component per se active component, is 80% of 12.5 wt. % or 10.0 wt. %. Thus, the weight percent ranges set forth in this specification relate to the components per se (active component).

The broad-spectrum disinfectant compositions of the present invention are very effective in eradicating vegetative bacteria such as *Pseudomonas aeruginosa, Staphylococcus aureus, Salmonella enterica* and *Enterococcus hirae*. The compositions have surprisingly been found to be very effective against various spore-forming fungi such as *Aspergillus niger, Aspergillus brasiliensis*, and *Trichophyton mentagrophytes*. The compositions have also been found to be effective against yeast such as *Candida albicans* and furthermore have also been found to be effective against mycobacterium such as *Mycobacterium terrae*.

In order to achieve good properties of the present invention as noted herein, various compounds that are detrimental thereto are avoided. That is, the cleaning composition is free thereof, i.e. contains no such compounds. One such group of compounds is various chelants that are alkylamine polyacetic acid compounds that contain three or more acetic acid groups such as ethylenediamine tetraacetic acid (EDTA), hydroxy-ethylethylenediamine triacetic acid (HEDTA), ethylene triaminepentaacetic acid, and similar compounds. Such compounds have an adverse effect and the use thereof is limited in some European countries. If utilized, the amount thereof is very small such as less than about 1.0 wt. %, desirably less than about 0.5 wt. % and preferably less than about 0.1 wt. % based upon the total weight of the cleaning composition.

Other compounds that are avoided, i.e. the compositions of the present inventor are generally free thereof, include phenol (negative safety profile) and various derivatives thereof, zwitterionic detergents (e.g. betaines), and glycol ether solvents, since they generally impede performance, efficacy, etc. If utilized, the listed compounds are each incorporated in very small amounts such as about 1 wt. % or less, desirably about 0.5 wt. % or less, and preferably about 0.3 wt. % or less based upon the total weight of the cleaning composition.

The invention will be better understood by reference to the following examples which serve to illustrate but not to limit the present invention.

The various above-noted components of the present invention can generally be added in any order to form the broad spectrum disinfectant composition of the present invention except that potentially flammable compounds such as n-propyl alcohol and the alkyl ammonium halogen are added last. While the mixing order of the components can vary, the following mixing order is recommended. Initially, a majority of the deionized water should be added to the mixing vessel followed by the surfactants (octyldimethylamine oxide or the ethoxylated nonionic surfactants coco amine 15EO and coco amine 2EO). There may be some gelling or haze when coco amine 2 EO is added, but it will mix in completely with adequate time and agitation. After the surfactants are completely mixed into the batch, ethanolamine and the chelant should be added. Due to flammability concerns, DDAC should be the second-to-last ingredient added to the batch, and n-propyl alcohol should be the final ingredient added to the batch.

Example 1

Effect of Chelant/Sequestrant on Activity Against *A. brasiliensis* 16404

Examples A through F were tested against *A. brasiliensis* 16404. The results are set forth in FIG. 1. Data from FIG. 1 was obtained using ASTM International (2003) Standard Guide for Assessment of Antimocrobial Activity Using a Time-Kill Procedure, document #E2315-03. As apparent from FIG. 1, all of the various chelants were effective in producing average log reductions generally at least 10 times greater than the Control wherein no chelant/sequestrant was utilized.

TABLE 1

| Chemical Name | Brand Name | Formulation # | | | | | |
|---|---|---|---|---|---|---|---|
| | | A | B | C | D | E | F |
| Water | Water | 75.50 | 73.50 | 73.50 | 73.50 | 73.50 | 73.50 |
| Didecyl dimethyl ammonium chloride (80%) | Bardac 2280 | 12.50 | 12.50 | 12.50 | 12.50 | 12.50 | 12.50 |
| Secondary alchohol ethoxylate | Tergitol 15-S-7 | 4.00 | 4.00 | 4.00 | 4.00 | 4.00 | 4.00 |
| Polyether polyol | Tergitol L-61 | 8.00 | 8.00 | 8.00 | 8.00 | 8.00 | 8.00 |
| Chelant/Sequestrant | | None | 2% MGDA | 2% EDDS | 2% IDSA | 2% GLDA | 2% Carboxy methyl Inulin |

Example 2

The amount of DDAC was varied from none to 25 wt. % and the nonionic coupling agent was an ethylene oxide/propylene oxide block copolymer as set forth in Table 2. This composition was tested against *A. brasiliensis* 16404 and the results are set forth in FIG. 2. Data from FIG. 2 was obtained using a blend of two methods. Stainless steel disks described in ASTM International (2002), and standard quantitative disk carrier described in Test method for determining the bactericidal, virucidal, fungicidal, mycobactericidal and sporicidal activities of liquid chemical germicides, document #E2197-02, ASTM International, West Conshohocken, Pa. were utilized as a modification to BS EN 13697:2001 Quantitative non-porous surface test for the evaluation of bactericidal and/or fungicidal activity of chemical disinfectants used in food, industrial, domestic and institutional areas—test method and requirements without mechanical action (Phase 2, step 2). As apparent from FIG. 2, effective results were obtained generally when the weight percent of DDAC was generally greater than about 8% up to about 25 wt. %.

TABLE 2

| Chemical Name | Brand Name | Formulation # | | | | | | | | | |
|---|---|---|---|---|---|---|---|---|---|---|---|
| | | A | B | C | D | E | F | G | H | I | J |
| Water | Water | 87.00 | 86.00 | 85.00 | 84.00 | 83.00 | 82.00 | 77.00 | 71.65 | 67.00 | 62.00 |
| Didecyl dimethyl ammonium chloride (80%) | Bardac 2280, BTC 1010-80% | 0.00 | 1.00 | 2.00 | 3.00 | 4.00 | 5.00 | 10.00 | 15.35 | 20.00 | 25.00 |
| Ethylene oxide/ Propylene oxide block copolymer | Pluronic 10R5 | 2.00 | 2.00 | 2.00 | 2.00 | 2.00 | 2.00 | 2.00 | 2.00 | 2.00 | 2.00 |

TABLE 2-continued

| Chemical Name | Brand Name | Formulation # | | | | | | | | | |
|---|---|---|---|---|---|---|---|---|---|---|---|
| | | A | B | C | D | E | F | G | H | I | J |
| Ethanolamine | Ethanolamine | 6.00 | 6.00 | 6.00 | 6.00 | 6.00 | 6.00 | 6.00 | 6.00 | 6.00 | 6.00 |
| N-Propyl Alcohol | N-Propyl Alcohol | 5.00 | 5.00 | 5.00 | 5.00 | 5.00 | 5.00 | 5.00 | 5.00 | 5.00 | 5.00 |

Figure 3:
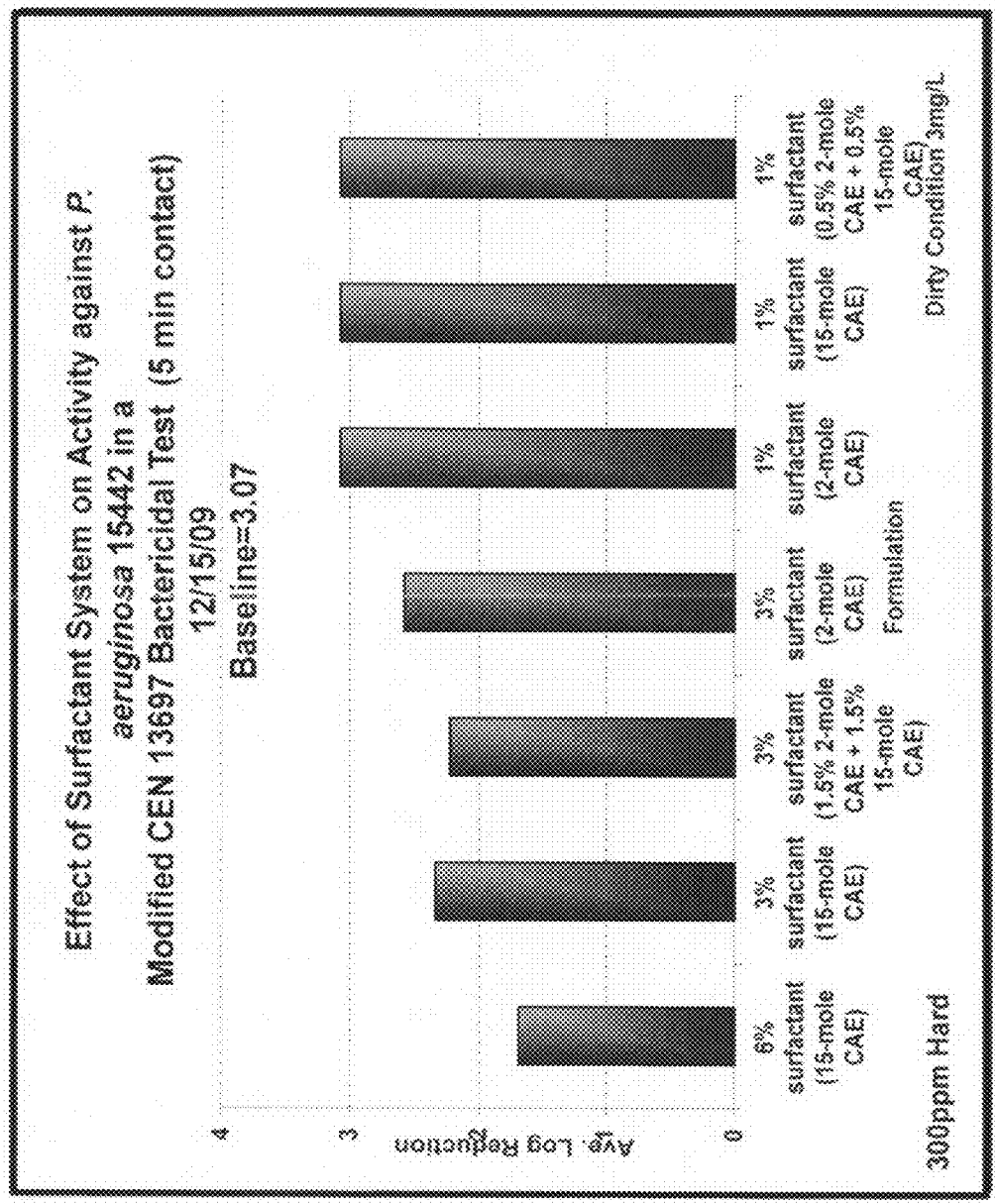
FIG. 3 is a chart showing the impact of concentration and HLB values with respect to efficacy against *Pseudomonas aeruginosa* 15442.

FIG. 3 relates to Table 3, wherein the amounts of water were varied, as were the amounts of Coco amine 2 EO and Coco amine 15 EO. These compositions were tested against *P. aeruginosa* 15442. Data from FIG. 3. was obtained using a modified BS EN 13697:2001 Quantitative non-porous surface test for the evaluation of bactericidal and/or fungicidal activity of chemical disinfectants used in food, industrial, domestic and institutional areas—test method and requirements without mechanical action (Phase 2, step 2). As apparent from FIG. 3, either the cocamine 15EO or the cocamine 2EO or both were utilized in low amounts, that is generally a total of 3 wt. % or less.

TABLE 3

| Chemical Name | Brand Name | Formulation # | | | | | | |
|---|---|---|---|---|---|---|---|---|
| | | A | B | C | D | E | F | H |
| Water | Water | 70.50 | 73.50 | 73.50 | 73.50 | 75.50 | 75.50 | 75.50 |
| Didecyl dimethyl ammonium chloride (80%) | Bardac 2280 | 12.50 | 12.50 | 12.50 | 12.50 | 12.50 | 12.50 | 12.50 |
| N-Propyl Alcohol | N-Propyl Alcohol | 6.00 | 6.00 | 6.00 | 6.00 | 6.00 | 6.00 | 6.00 |
| Ethanolamine | Ethanolamine | 5.00 | 5.00 | 5.00 | 5.00 | 5.00 | 5.00 | 5.00 |
| Cocamine 2 EO | Toximul CA-2 | 0.00 | 0.00 | 1.50 | 3.00 | 1.00 | 0.00 | 0.50 |
| Cocamine 15 EO | Ethomeen C25A | 6.00 | 3.00 | 1.50 | 0.00 | 0.00 | 1.00 | 0.50 |

Figure 2:
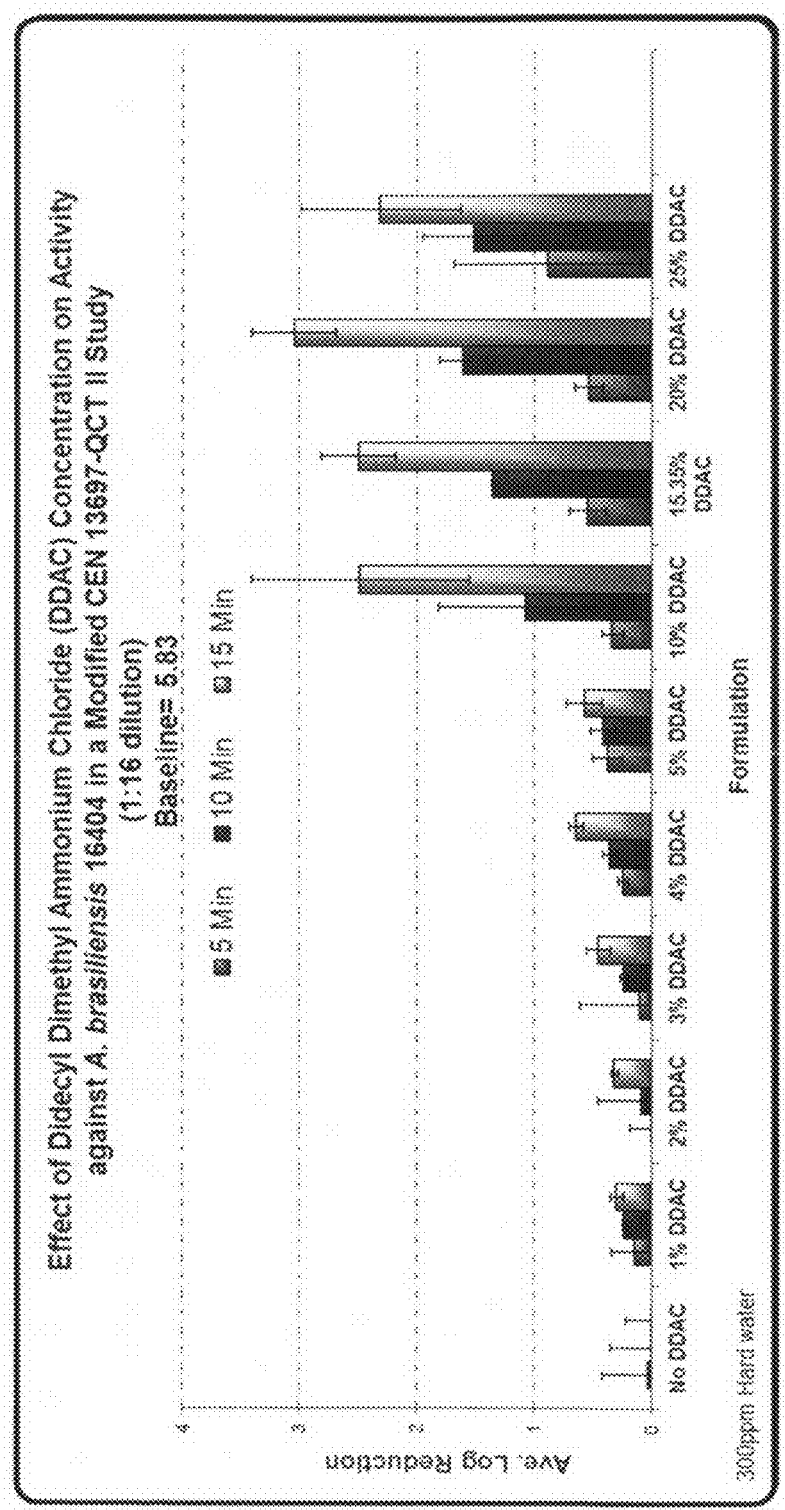
FIG. 2 is a chart showing the effect of varying concentration levels of the quat DDAC against *Aspergillus brasiliensis* 16404.

The compositions utilized with regard to FIGS. 1, 2, and 3 were very stable with respect to the didecyl dimethyl ammonium chloride. These compositions also had very stable post-gamma-irradiation with respect to the didecyl dimethyl ammonium chloride even after dilution with deionized water to normal use concentrations (e.g. 1:128). The compositions also had excellent fungicidal efficacy.

Fungicidal testing was performed as outlined in AOAC Official Method 955:17: AOAC Fungicidal Activity of Disinfectants (Official Methods of Analysis, Eighteenth edition, 2006), against *Trichophyton mentagrophytes* ATCC 9533: *Aspergillus brasiliensis* ATCC 16404 and *Aspergillus niger* ATCC 6275. The broad-spectrum disinfectant composition was that as set forth in Table A and the use concentration was 1:64 for *Aspergillus niger* 16404 and 1:128 for *Aspergillus niger* 6275 and *Trichophyton mentagrophytes* 9533.

Table 4 summarizes the achieved fungicidal data.

TABLE 4

| Microorganism species | Product batch | Results |
|---|---|---|
| **Aspergillus brasiliensis* 16404 | A | No growth* |
| | B | No growth* |
| *Aspergillus niger* 6275 | A | No growth* |
| | B | No growth* |

TABLE 4-continued

| Microorganism species | Product batch | Results |
|---|---|---|
| *Trichophyton mentagrophytes* 9533 | A | No growth* |
| | B | No growth* |
| | C | No growth* |

*No fungal growth was seen when the subculture tubes were streaked eliminating fungistasis as the reason of lack of growth in these tubes.
**Formerly *Aspergillus niger* 16404

The compositions of the present invention also have excellent bactericidal efficacy. Bactericidal testing was performed utilizing the AOAC Official Methods 955.14, Use-Dilution Methods: Testing Disinfectants against *Salmonella choleraesuis;* 955:15. Testing Disinfectants against *Staphylococcus aureus*, and 964.02 Testing Disinfectants against *Pseudomonas aeruginosa* (Official Methods of Analysis, Eighteenth edition, 2006).

Table 5 shows the bactericidal activity of the composition of Table A.

TABLE 5

| Microorganism species | Product batch | Dilution | Positive Tubes vs. Total Tubes |
|---|---|---|---|
| *Pseudomonas aeruginosa* ATCC 15442 | A | 1:128 | 0/60 |
| | B | 1:128 | 0/60 |
| | C | 1:128 | 0/60 |
| **Salmonella enterica* ATCC 10708 | A | 1:128 | 0/60 |
| | B | 1:128 | 0/60 |
| | C | 1:128 | 0/60 |
| *Staphylococcus aureus* ATCC 6538 | A | 1:128 | 0/60 |
| | B | 1:128 | 0/60 |
| | C | 1:128 | 0/60 |

*Formerly *Salmonella Choleraesuis* ATCC 10708

A positive tube means "growth" of a vegetative bacteria and 0/60 means that no growth in any of the 60 tubes was determined. That is, the disinfectant completely killed the organism in all the test tubes.

The present invention has other many advantages that include good broad-spectrum microbial efficacy within normal use concentrations, and small environmental impact since the excipient ingredients (including surfactants, chelants, solvents) exhibit good proven biodegradability. Another advantage, as noted above, is the ability to be sterilized by using gamma-irradiation to provide a sterile composition for clean room applications. For example, the concentrated liquid composition is physically stable even when exposed to gamma-irradiation and the use-dilution is physically stable for 5 weeks minimum. The table below shows the bactericidal activity of the use-dilution of the composition D of Table A after 5 weeks.

TABLE 6

| Microorganism species | Product batch | Dilution | Positive Tubes vs. Total Tubes |
|---|---|---|---|
| Pseudomonas aeruginosa ATCC 15442 | A | 1:128 | 0/10 |
| | B | 1:128 | 0/10 |
| *Salmonella enterica ATCC 10708 | A | 1:128 | 0/10 |
| | B | 1:128 | 0/10 |
| Staphylococcus aureus ATCC 6538 | A | 1:128 | 0/10 |
| | B | 1:128 | 0/10 |

*Formerly Salmonella choleraesuis ATCC 10708

Samples of the composition D of Table A were gamma-irradiated at 40-45 kGy, and then stored at a predetermined temperature for a period of time prior to testing. Results of this stability study are shown in Table 7. All results show that no degradation of the product, and specifically the quaternary ammonium chloride concentration, occurred post-irradiation at three months at 40° C.

TABLE 7

| | Initial | 1-month at 40° C. | 3-months at 40° C. |
|---|---|---|---|
| Appearance | Clear, homogeneous liquid | Clear, homogeneous liquid | Clear, homogeneous liquid |
| Specific Gravity | 0.985 | 0.986 | 0.985 |
| Didecyldimethyl Ammonium Chloride Concentration (wt %) | 9.9 | 10.0 | 10.0 |

While in accordance with the patent statutes, the best mode and preferred embodiment have been set forth, the scope of the invention is not limited thereto, but rather by the scope of the attached claims.

What is claimed is:

1. A broad spectrum liquid cleaning composition, comprising:
 a quaternary ammonium halogen comprising a first dialkyl wherein each alkyl, independently, has from 1 to about 7 carbon atoms, and a second dialkyl wherein each said alkyl, independently, has from about 8 to about 25 carbon atoms; or an N-alkyl dimethyl benzyl ammonium chloride wherein said alkyl has from about 12 to about 18 carbon atoms; or an N-alkyl dimethyl ethyl benzyl ammonium chloride wherein said alkyl has from 12 to about 18 carbon atoms, or any combination thereof;
 an alkaline agent comprising an organic alcohol amine, a strong base, sodium carbonate, or sodium bicarbonate, or an combination thereof;
 optionally a chelant comprising an alkylglycine organic acid, an iminodisuccinic acid or a derivative thereof, an ethylendiaminedisuccinate or a derivative thereof, a carboxylmethyl inulin or a derivative thereof, or glutamic acid N,N-diacetic acid, or any combination thereof;
 a nonionic surfactant coupler or at least one alkoxylated nonionic surfactant, or both; and
 a solvent system comprising water, or an aliphatic alcohol, or both.

2. The broad spectrum liquid cleaning composition of claim 1, wherein the pH of the composition is from about 7 to about 13.

3. The broad spectrum liquid cleaning composition of claim 2, wherein the quaternary ammonium halogen is present in an amount from about 5 wt. % to about 25 wt. % based upon the total weight of the cleaning composition, wherein the alkaline agent is present in an amount from about 3 wt. % to about 10 wt. % based on the total weight of the composition, wherein the optional chelant when present is in an amount from about 0.2 wt. % to about 3.0 wt. % based on the total weight of the cleaning composition, wherein the nonionic surfactant coupler is present in an amount from about 0.2 wt. % to about 5.0 wt. % based on the total weight of the cleaning composition; and wherein the at least one alkoxylated nonionic surfactant is an amine alkoxylated surfactant having from about 2 to about 20 repeat units of an alkylene oxide in an amount from about 0.4 wt. % to about 4.0 wt. %, or at least one alcohol alkoxylated nonionic surfactant in an amount of from about 0.1 wt. % to about 10 wt. %, or at least one block copolymer of ethylene oxide-propylene oxide in an amount of from about 0.4 wt. % to about 4.0 wt. %, based upon the total weight of the cleaning composition.

4. The broad spectrum liquid cleaning composition of claim 3, wherein the quaternary ammonium halogen is present in an amount from about 7 wt. % to about 20 wt. % based upon the total weight of the cleaning composition, wherein the alkaline agent is present in an amount from about 4 wt. % to about 9 wt. % based on the total weight of the composition, wherein the chelant is present in an amount from about 0.6 wt. % to about 3.0 wt. % based on the total weight of the cleaning composition, wherein the nonionic surfactant coupler is present in an amount from about 0.5 wt. % to about 5.0 wt. % based on the total weight of the cleaning composition; and wherein the amine alkoxylated nonionic surfactant comprises at least two compounds, one said amine alkoxylated compound having a high HLB value of from about 12 to about 24 and at least one said amine alkoxylated compound having a low HLB value of from about 2 to about 11.

5. The broad spectrum liquid cleaning composition of claim 4, wherein the quaternary ammonium halogen is present in an amount from about 8 wt. % to about 15 wt. % based upon the total weight of the cleaning composition, wherein the alkaline agent is present in an amount from about 5 wt. % to about 8 wt. % based on the total weight of the composition, wherein the chelant is present in an amount from about 0.8 wt. % to about 3.0 wt. % based on the total weight of the cleaning composition, wherein the nonionic surfactant coupler is present in an amount from about 0.75 wt. % to about 5.0 wt. % based on the total weight of the cleaning composition; and wherein the high HLB amine alkoxylate has an HLB value of from about 14 to about 20 and is present in an amount of from about 0.2 to about 2.0 wt. % based upon the total weight of the cleaning composition, wherein the low HLB amine alkoxylated compound has a HLB value of from about 3 to about 8 and is present in an amount of from about 0.2 to about 2.0 wt. % based upon the total weight of the cleaning composition, and wherein the pH of the composition is from about 9 to about 13.

6. The broad spectrum liquid cleaning composition of claim 2, wherein the quaternary ammonium halogen comprises a dioctyl dimethyl ammonium chloride, didecyl dimethyl ammonium chloride, N-alkyl($C_{12}$-$C_{18}$)dimethyl benzyl ammonium chloride, or N-alkyl($C_{12}$-$C_{18}$)dimethyl ethylbenzyl ammonium chloride, or any combination thereof;
   wherein the alkaline agent comprises a monoethanol amine, triethanol amine, sodium hydroxide, potassium hydroxide, sodium carbonate, or sodium bicarbonate, or any combination thereof;
   wherein the aliphatic alcohol has from 2 to about 8 carbon atoms and is present in an amount from about 2 to about 20 wt. % based on the total weight of the cleaning composition;
   wherein the nonionic surfactant coupler comprises at least one alkyl amine oxide having from about 6 to about 14 carbon atoms; and
   wherein the alkoxylated nonionic surfactant comprises an amine alkoxylated nonionic surfactant, an alkoxylated block copolymer, or an alcohol alkoxylated nonionic surfactant, or any combination thereof.

7. The broad spectrum liquid cleaning composition of claim 2, wherein the quaternary ammonium halogen comprises a dioctyl dimethyl ammonium chloride, didecyl dimethyl ammonium chloride, N-alkyl($C_{12}$-$C_{18}$)dimethyl benzyl ammonium chloride, or N-alkyl($C_{12}$-$C_{18}$)dimethyl ethylbenzyl ammonium chloride, or any combination thereof;
   wherein the alkaline agent comprises monoethanol amine, triethanol amine, sodium hydroxide, potassium hydroxide, sodium carbonate, or sodium bicarbonate, or any combination thereof;
   wherein the aliphatic alcohol has from 2 to about 4 carbon atoms and is present in an amount from about 2 to about 20 wt. % based on the total weight of the cleaning composition;
   including the chelant, the chelant comprising an alkylglycine organic acid, and iminodisuccinic acid, an ethylene diaminedisuccinate, a carboxymethyl inulin, or glutamic acid N,N-diacetic acid, or any combination thereof; and
   wherein the nonionic surfactant coupler comprises at least one alkyl amine oxide having from about 6 to about 14 carbon atoms; and
   wherein the alkoxylated nonionic surfactant comprises an amine alkoxylated nonionic surfactant, an alkoxylated block copolymer, or an alcohol alkoxylated nonionic surfactant, or any combination thereof.

8. The broad spectrum liquid cleaning composition of claim 5, wherein the quaternary ammonium halogen comprises a dioctyl dimethyl ammonium chloride, didecyl dimethyl ammonium chloride, N-alkyl($C_{12}$-$C_{18}$)dimethyl benzyl ammonium chloride, or N-alkyl($C_{12}$-$C_{18}$), dimethyl ethylbenzyl ammonium chloride, or any combination thereof;
   wherein the alkaline agent comprises a monoethanol amine, triethanol amine, sodium hydroxide, potassium hydroxide, sodium carbonate, and sodium bicarbonate, or any combination thereof;
   wherein the aliphatic alcohol has from 2 to about 4 carbon atoms and is present in an amount from about 3 to about 9 wt. % based on the total weight of the cleaning composition;
   wherein said chelant is methylglycine diacetic acid; and
   wherein the nonionic surfactant coupler comprise at least one alkyl amine oxide having from about 6 to about 14 carbon atoms.

9. The broad spectrum liquid cleaning composition of claim 1, wherein the liquid cleaning composition exhibits no degradation upon exposure to gamma-irradiation.

10. The broad spectrum liquid cleaning composition of claim 3, wherein said liquid cleaning composition exhibits no degradation upon exposure from about 40 to about 45 kGy after at least about 5 weeks.

11. The broad spectrum liquid cleaning composition of claim 6, wherein said liquid cleaning composition exhibits no degradation upon exposure from about 40 to about 45 kGy after at least about 5 weeks.

12. The broad spectrum liquid cleaning composition of claim 5, wherein said liquid cleaning composition exhibits no degradation upon exposure from about 40 to about 45 kGy after at least about 3 months.

13. The broad spectrum liquid cleaning composition of claim 8, wherein said liquid cleaning composition exhibits no degradation upon exposure from about 40 to about 45 kGy after at least about 3 months.

14. The broad spectrum liquid cleaning composition of claim 6, wherein the quaternary ammonium halogen is didecyl dimethyl ammonium chloride.

15. A process for forming a broad spectrum liquid cleaning composition, comprising the steps of:
   mixing in any order a quaternary ammonium halogen comprising a first dialkyl wherein each alkyl, independently, has from 1 to about 7 carbon atoms, and a second dialkyl wherein each said alkyl, independently, has from about 8 to about 25 carbon atoms; or an N-alkyl dimethyl benzyl ammonium chloride wherein said alkyl has from about 12 to about 18 carbon atoms; or an N-alkyl dimethyl ethyl benzyl ammonium chloride wherein said alkyl has from 12 to about 18 carbon atoms, or any combination thereof;
   an alkaline agent comprising an organic alcohol amine, a strong base, sodium carbonate, or sodium bicarbonate, or an combination thereof;
   optionally a chelant comprising an alkylglycine organic acid, an iminodisuccinic acid or a derivative thereof, an ethylendiaminedisuccinate or a derivative thereof, a carboxylmethyl inulin or a derivative thereof, or glutamic acid N,N-diacetic acid, or any combination thereof;
   a nonionic surfactant coupler or at least one alkoxylated nonionic surfactant, or both; and
   a solvent system comprising water, or an aliphatic alcohol, or both.

16. The process of claim 15, wherein the quaternary ammonium halogen is present in an amount from about 5 wt. % to about 25 wt. % based upon the total weight of the cleaning composition, wherein the alkaline agent is present in an amount from about 3 wt. % to about 10 wt. % based on the total weight of the composition, wherein the optional chelant when present is in an amount from about 0.2 wt. % to about 3.0 wt. % based on the total weight of the cleaning composition, wherein the nonionic surfactant coupler is present in an amount from about 0.2 wt. % to about 5.0 wt. % based on the total weight of the cleaning composition; and wherein the at least one alkoxylated nonionic surfactant is an amine alkoxylated surfactant having from about 2 to about 20 repeat units of an alkylene oxide in an amount from about 0.4 wt. % to about 4.0 wt. %, or at least one alcohol alkoxylated nonionic surfactant in an amount of from about 0.1 wt. % to about 10 wt. %, or at least one block copolymer of ethylene oxide-propylene oxide in an amount of from about 0.4 wt. % to about 4.0 wt. %, based upon the total weight of the cleaning composition.

17. The process of claim 16, wherein the quaternary ammonium halogen is present in an amount from about 7 wt. % to about 20 wt. % based upon the total weight of the cleaning composition, wherein the alkaline agent is present in an amount from about 4 wt. % to about 9 wt. % based on the total weight of the composition, wherein the chelant is present in an amount from about 0.6 wt. % to about 3.0 wt. % based on the total weight of the cleaning composition, wherein the nonionic surfactant coupler is present in an amount from about 0.5 wt. % to about 5 wt. % based on the total weight of the cleaning composition; and wherein the amine alkoxylated nonionic surfactant comprises at least two compounds, one said amine alkoxylated compound having a high HLB value of from about 12 to about 24 and at least one said amine alkoxylated compound having a low HLB value of from about 2 to about 11.

18. The process of claim 16, wherein the quaternary ammonium halogen comprises a dioctyl dimethyl ammonium chloride, didecyl dimethyl ammonium chloride, N-alkyl($C_{12}$-$C_{18}$)dimethyl benzyl ammonium chloride, or N-alkyl($C_{12}$-$C_{18}$)dimethyl ethylbenzyl ammonium chloride, or any combination thereof;

wherein the alkaline agent comprises a monoethanol amine, triethanol amine, sodium hydroxide, potassium hydroxide, sodium carbonate, or sodium bicarbonate, or any combination thereof;

wherein the aliphatic alcohol has from 2 to about 8 carbon atoms and is present in an amount from about 2 to about 20 wt. % based on the total weight of the cleaning composition;

wherein the chelant is present and comprises an alkylglycine organic acid, an iminodisuccinic acid, a carboxymethyl inulin, or a glutamic acid N,N-diacetic acid; or any combination thereof;

wherein the nonionic surfactant coupler comprises at least one alkyl amine oxide having from about 6 to about 14 carbon atoms; and wherein the alkoxylated nonionic surfactant comprises an amine alkoxylated nonionic surfactant, an alkoxylated block copolymer, or an alcohol alkoxylated nonionic surfactant, or any combination thereof.

19. The process of claim 17, wherein initially said water is added to mixing vessel and subsequently said chelant and said nonionic surfactant coupler are added; subsequently adding said alkaline agent and said chelant; then adding said quaternary ammonium halogen and thereafter adding said optional aliphatic alcohol.

\* \* \* \* \*